(12) United States Patent
Furusawa et al.

(10) Patent No.: US 7,593,111 B2
(45) Date of Patent: Sep. 22, 2009

(54) SENSOR APPARATUS

(75) Inventors: Kentaro Furusawa, Tokyo (JP);
Natsuhiko Mizutani, Tokyo (JP); Ryo Kuroda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/174,776

(22) Filed: Jul. 17, 2008

(65) Prior Publication Data
US 2009/0021742 A1 Jan. 22, 2009

(30) Foreign Application Priority Data
Jul. 18, 2007 (JP) .............................. 2007-187089

(51) Int. Cl.
*G01N 21/55* (2006.01)
(52) U.S. Cl. ...................................... 356/445; 356/448
(58) Field of Classification Search ......... 356/445–448; 385/37, 12, 30; 422/82.05, 82.11; 372/96, 372/45.01–46.016, 26, 28, 38.01–38.02, 372/32
See application file for complete search history.

(56) References Cited

U.S. PATENT DOCUMENTS

| 5,946,336 A | 8/1999 | Mizutani et al. ............... 372/50 |
| 6,337,868 B1 | 1/2002 | Mizutani ...................... 372/27 |
| 7,349,598 B2 | 3/2008 | Matsumura ................... 385/37 |

FOREIGN PATENT DOCUMENTS
JP 2005-257458 A 9/2005

*Primary Examiner*—Michael A Lyons
*Assistant Examiner*—Tri T Ton
(74) *Attorney, Agent, or Firm*—Fitzpatrick, Cella, Harper & Scinto

(57) ABSTRACT

A plasmon sensor apparatus using a metallic fine periodic structure designed to reduce the dependences of the resonance wavelength and sensitivity on the incident angle. The plasmon sensor apparatus has a sensing element including a metallic member having periodic slit openings and metallic portions, and a substrate on which the metallic member is held, a light source which emits light so that the light is incident on the sensing element, and a photodetector which detects light obtained from the light source. If the period of the slit openings is Λ; the width of the metallic portions is d; and the thickness of the metallic member is h, the aspect ratio h/(Λ−d) of the slit openings is 3 or higher and the opening width (Λ−d) is equal to or smaller than the wavelength of light applied from the light source to the sensing element.

7 Claims, 7 Drawing Sheets

SENSOR APPARATUS

BACKGROUND OF THE INVENTION

1. Field of the Invention

The present invention relates to a sensor apparatus using a metallic fine periodic structure and used for monitoring, by utilizing surface plasmon resonance (SPR), environmental changes accompanied with changes in dielectric response in the vicinity of a surface or changes in a surface condition due to antigen-antibody reaction or the like.

2. Description of the Related Art

Sensors utilizing surface plasmon resonance utilize surface plasmon polaritons (SPPs) existing at an interface between a metal and a dielectric.

SPPs at a flat plane interface have an electric field distribution in a space of several hundred nanometers in the vicinity of the surface. Therefore a sensor using SPPs finds application as a refractive index sensor sensitive in the vicinity of a surface.

In ordinary cases, there is a need to achieve phase alignment between incident light and SPPs for excitation of SPPs, and an oblique incidence construction through a prism, e.g., one using a Kretchmann configuration is adopted.

On the other hand, a unit in which a periodic fine structure formed of a metal is provided on the above-described interface instead of a metallic flat surface to achieve phase alignment between incident light and SPPs is also known widely (Japanese Patent Application Laid-Open No. 2005-257458).

Plasmon sensors using a conventional metallic fine periodic structure utilize a construction for observing a change in plasmon resonance spectrum as a sensor response and have such a characteristic that the resonance wavelength and sensitivity in such a case depend largely on the incident angle. Advantageously, this means that the resonance wavelength can be optimized by adjusting the incident angle in a case where a small-line-width light source such as a laser is used. On the other hand, the sensitivity is limited by diffraction of incident light itself unless a sufficiently-collimated large beam is used. There is, therefore, a problem that the degree of freedom with which a measuring optical system is designed is low. There is also a problem that the response is sensitive to alignment errors.

It is, therefore, an object of the present invention is to provide a plasmon sensor apparatus using a metallic fine periodic structure and capable of reducing the dependence of the resonance wavelength and sensitivity on the incident angle, increasing the degree of freedom with which a measuring optical system is designed, and increasing an alignment tolerance margin.

SUMMARY OF THE INVENTION

The present invention is directed to a sensor apparatus comprising: a sensing element including a metallic member having periodic slit openings and metallic portions, and a substrate on which the metallic member is held; a light source which emits light so that the light is incident on the sensing element; and a photodetector which detects light obtained from the light source, wherein if the period of the slit openings is $\Lambda$; the width of the metallic portions is d; and the thickness of the metallic member is h, the aspect ratio $h/(\Lambda-d)$ of the slit openings is 3 or higher and the opening width ($\Lambda-d$) is equal to or smaller than the wavelength of the light applied from the light source to the sensing element.

The aspect ratio can be within the range from 4 to 8.

The opening width ($\Lambda-d$) can be equal to or smaller than ⅓ of the wavelength of light applied from the light source. The opening width ($\Lambda-d$) is smaller than 100 nm.

The proportion of the metallic portions in the metallic member can be equal to or larger than 80% and lower than 90%.

The light can be introduced from the substrate side of the sensing element.

The sensor apparatus can utilize plasmon resonance.

According to the present invention, the incident angle dependences of the resonance wavelength and sensitivity of a plasmon resonance sensor apparatus using a metallic fine periodic structure can be reduced. The degree of freedom with which a measuring optical system is designed is thereby improved. An alignment tolerance margin can also be increased.

Further features of the present invention will become apparent from the following description of exemplary embodiments with reference to the attached drawings.

DESCRIPTION OF THE EMBODIMENTS

The above-described sensor apparatus of the present invention includes a metallic fine periodic structure forming slits, a sensing element having a substrate on which the metallic fine periodic structure is held, a light source which emits light so that the light is incident on the sensing element and a detector for measuring light transmitted through or reflected by the sensing element. The sensor apparatus includes setting the width of each slit to value substantially equal to or smaller than the wavelength of light incident on the sensing element and setting the aspect ratio of the slit to 3 or higher.

The present invention includes a sensor apparatus having an adhesive layer provided between a fine periodic structure formed of a metallic member and a substrate to fix the metallic fine periodic structure on the substrate.

The present invention also includes a sensor apparatus into which light is introduced from the side of a substrate constituting a sensing element.

The number of waves of a surface plasmon can be expressed by

Formula 1

$$k_{sp} = \frac{2\pi}{\lambda}\sqrt{\frac{\varepsilon_1(\lambda)\varepsilon_m(\lambda)}{\varepsilon_1(\lambda)+\varepsilon_m(\lambda)}} \quad (1)$$

where $\varepsilon_1$ is the dielectric constant of a dielectric forming an interface with the metal, $\varepsilon_m$ is the dielectric constant of the metal, and $\lambda$ is the wavelength.

On the other hand, if scattering by the grating is considered, the number of waves of incident light can be expressed by Formula 2

$$k_{in} = \frac{2\pi}{\lambda}n_{in}\sin\theta_{in} - \frac{2\pi}{\Lambda} = k_0 n_{in}\sin\theta_{in} - \frac{2\pi}{\Lambda} \quad (2)$$

where $n_{in}$ is the incidence medium, $\theta_{in}$ is the incident angle, and $\Lambda$ is the period of the metallic fine structure (the period of the slit openings).

From the above, it can be understood that the surface plasmon is excited at a high efficiency at a wavelength at which $k_{sp}$ in equation (1) and $k_{in}$ in equation (2) coincide with each other. In a metallic slit structure, if the depth of slits is sufficiently large, plasmons in slit inner walls couple with each other and resonance thereof becomes dominant.

The transmission constant $\beta$ of this coupling mode with the case of infinitely deep slits satisfies the following dispersion formula.

Formula 3

$$\tanh\left[\sqrt{\beta^2 - k_0^2\varepsilon_d}\frac{a}{2}\right] = -\frac{\varepsilon_d\sqrt{\beta^2 - k_0^2\varepsilon_m}}{\varepsilon_m\sqrt{\beta^2 - k_0^2\varepsilon_d}} \quad (3)$$

where a is the width of the slits and $\varepsilon_d$ is the dielectric constant of the medium in the slits. A standing wave in this mode is formed by reflection at the opposite ends of the slits, and the resonance wavelength $\lambda_{CP}$ satisfies the following condition, depending on the refractive index of the reflecting interface.

Formula 4

$$\lambda_{CP} > \Lambda\sqrt{\frac{\varepsilon_1(\lambda)\varepsilon_m(\lambda)}{\varepsilon_1(\lambda)+\varepsilon_m(\lambda)}} \quad (4)$$

Figure 1A:
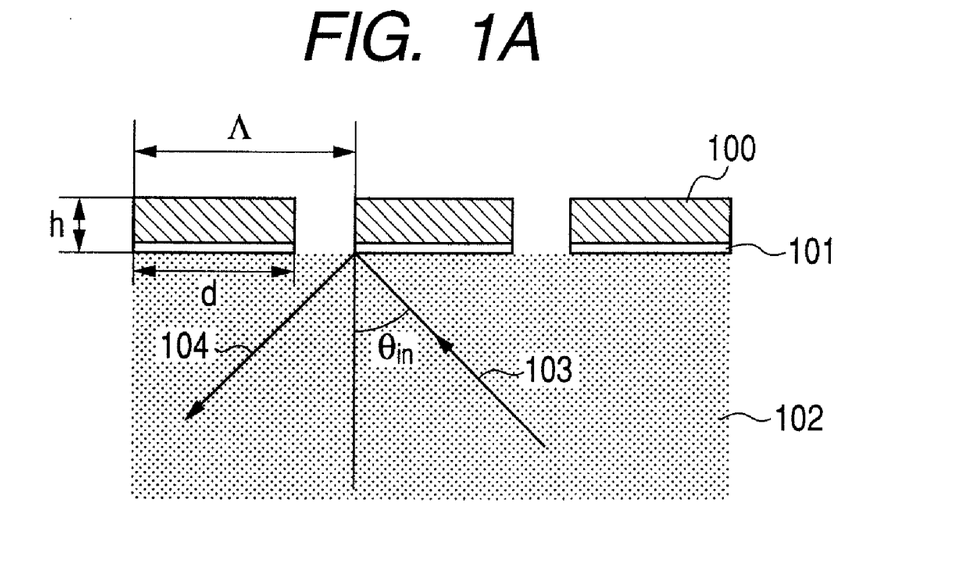
FIG. 1A is a diagram schematically illustrating a sensor head according to an embodiment of the present invention.

FIG. 1A illustrates a sensing head provided as a sensing element used in the present embodiment. The sensing head is constructed by fixing and holding a metallic fine periodic structure 100 on a substrate 102, with an adhesive layer 101 of an electroconductive oxide film or the like. A sensing medium formed of a dielectric is placed as an object to be monitored adjacent to the metallic fine periodic structure 100.

In the metallic fine periodic structure 100, rectangular metal portions having a predetermined width d and a height (thickness) h are unidimensionally disposed, i.e., arranged in one direction, with the period $\Lambda$. The periodic structure 100 may be seen as a rectangular slit opening is formed at a period $\Lambda$ in metallic member.

A filling factor f representing the proportion of the metal portions in the metallic member with respect to this metallic fine periodic structure 100 is f=d/$\Lambda$, and the aspect ratio q of the slit openings is q=h/($\Lambda$−d).

Figure 1B:
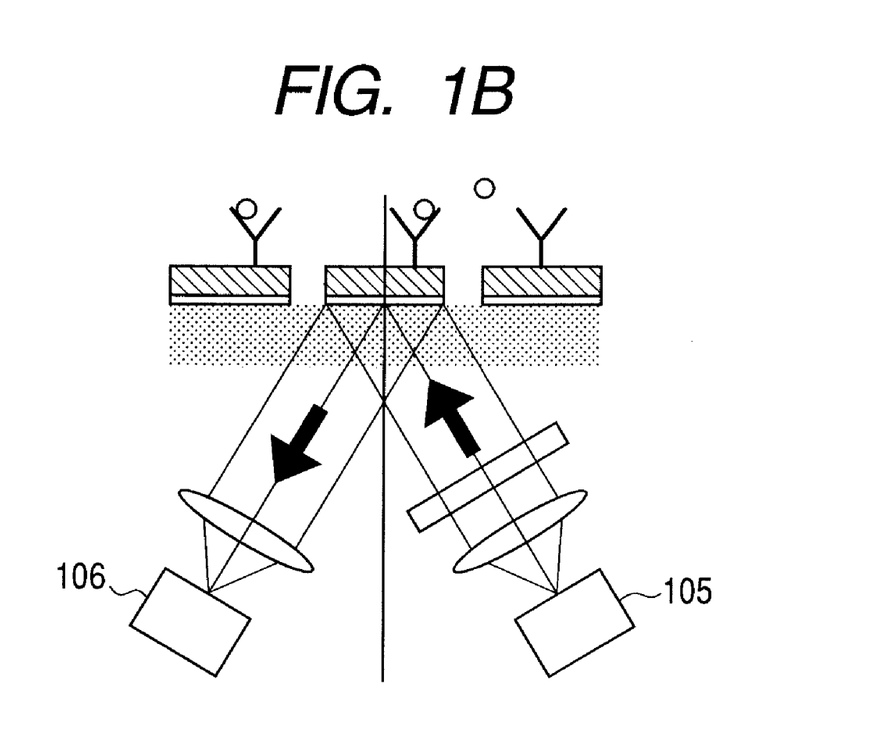
FIG. 1B is a diagram schematically illustrating the whole of a sensor apparatus.

As illustrated in FIG. 1B, illumination light 103 from a light source 105 is applied from the substrate 102 side to the sensing head at an incident angle $\theta_{in}$, and reflection light 104 from the sensing head is detected with a photodetector 106.

Through a change in this detection signal, a change in the sensing medium can be monitored. Detection of light transmitted through and traveling from the sensing head may alternatively be performed. The following description is made with respect to the case of detecting reflected light. However, the same description may apply to the case of detecting transmitted light.

In the present embodiment, the width ($\Lambda$−d) of the slit opening in the metallic fine periodic structure 100 is set to a sufficiently small value (<100 nm) and the slit depth h is also set to a sufficiently large value. The opening width ($\Lambda$−d) of the slit opening is ordinarily equal to or smaller than the wavelength of the light source. However, the opening width can be set equal to or smaller than preferably ⅓, more preferably ⅙ of the wavelength of the light source.

Plasmons in the wall surfaces opposed to each other forming the slits are made to couple with each other by setting the width of the slit opening to a small value and setting the slit depth of the slit opening to a sufficiently large value, thus enabling utilization of oozing-out of the coupled plasmon electromagnetic field into the slit.

As a result, the electric field distribution in each slit is thereby made uniform to improve the efficiency of coupling with a plane wave. Even in a case where oblique incidence is brought about, a deterioration in the efficiency of coupling with the incident plane wave is not considerable because the width of the slit is sufficiently smaller than the wavelength of the illumination light. Consequently, the angle dependence of the sensitivity is reduced.

Also, the resonance wavelength of the coupled plasmons is determined mainly by the structure, so that the dependence of the resonance wavelength on the incident can be reduced.

In the oblique incidence configuration, propagation-type surface plasmons on the substrate side and the surface side are excited. However, the energies of these plasmons decrease in inverse proportion to the incident angle. When the propagation-type surface plasmons couple with even-coupled plasmons in the slit, an electric field increasing effect can be obtained because the propagation-type surface plasmons on the substrate side and the surface side are excited in phase with each other. Consequently, the reduction in efficiency of coupling with a flat wave is limited and compensation for a reduction in sensor sensitivity is enabled.

Obtaining sufficiently narrow and deep slits capable of having such effects requires setting the width of the slit opening to a value substantially equal to or smaller than the wavelength of the light source. Also, for obtaining such slits, it is preferable to set the slit aspect ratio to 3 or higher. In particular, it is preferable to set the filling factor of the metallic fine periodic structure 100 equal to or higher than 80% and lower than 90%.

EXAMPLE AND COMPARATIVE EXAMPLE

The function of the present invention will be described more concretely with respect to an example of the invention.

Figure 2A:
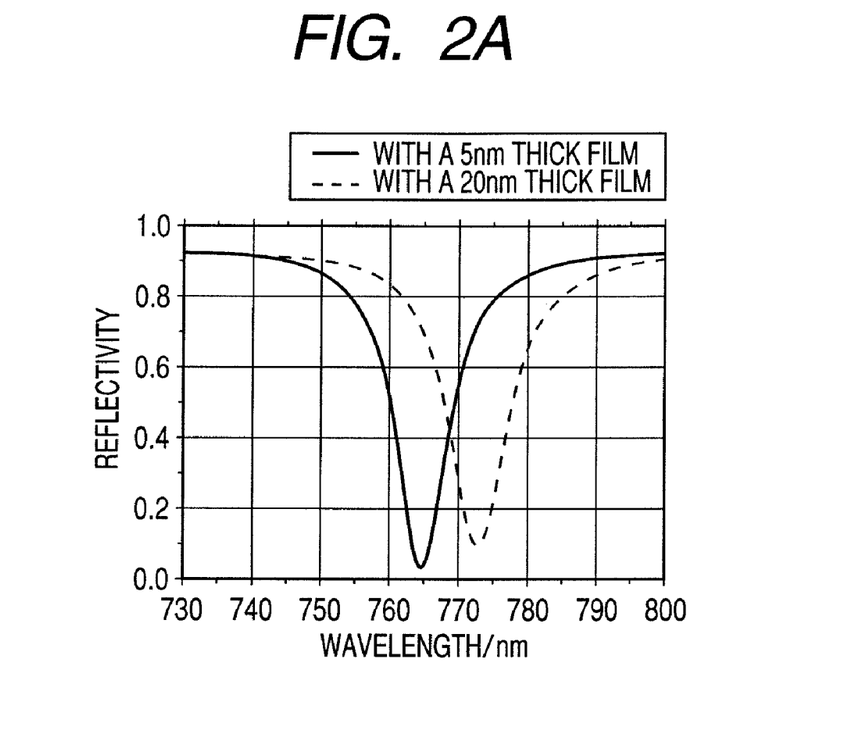
FIG. 2A is a graph illustrating a reflection spectrum with respect to direct incidence on a metallic fine periodic structure having $\Lambda$=500 nm, f=0.9 and h=80 nm.
Figure 2B:
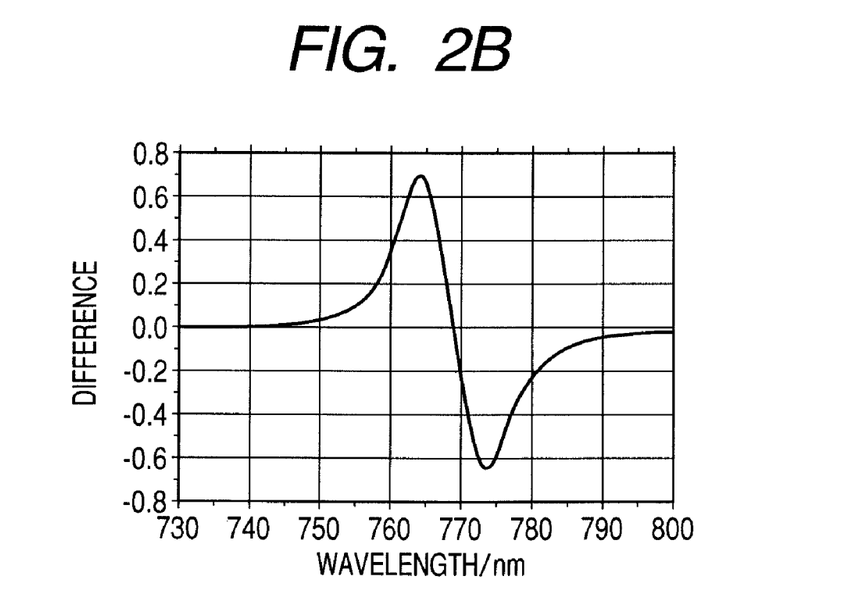
FIG. 2B is a graph illustrating a differential spectrum when the thickness of an applied thin film is changed.

A structure in which $\Lambda=500$ nm, f=0.9 and h=80 nm (aspect ratio q=1.6) will be considered as an example of surface plasmon response for comparison. That is, the width d of the metallic portion is 450 nm. FIG. 2A is a diagram illustrating a reflection spectrum with respect to direct incidence ($\theta_{in}=0$) in this case. A peak at a wavelength of about 760 nm is due to plasmon resonance. FIG. 2A illustrates a reflection spectrum (broken line) in a case where a thin film having a thickness of 20 nm at a refractive index of 1.57 is attached to the surface of the metallic fine periodic structure 100 and a reflection spectrum (solid line) in a case where a thin film having a thickness of 5 nm is attached. FIG. 2B illustrates a differential spectrum between these spectra as an index of sensitivity. The maximum of the difference between these spectra is defined as sensor sensitivity for the following description.

Figure 3:
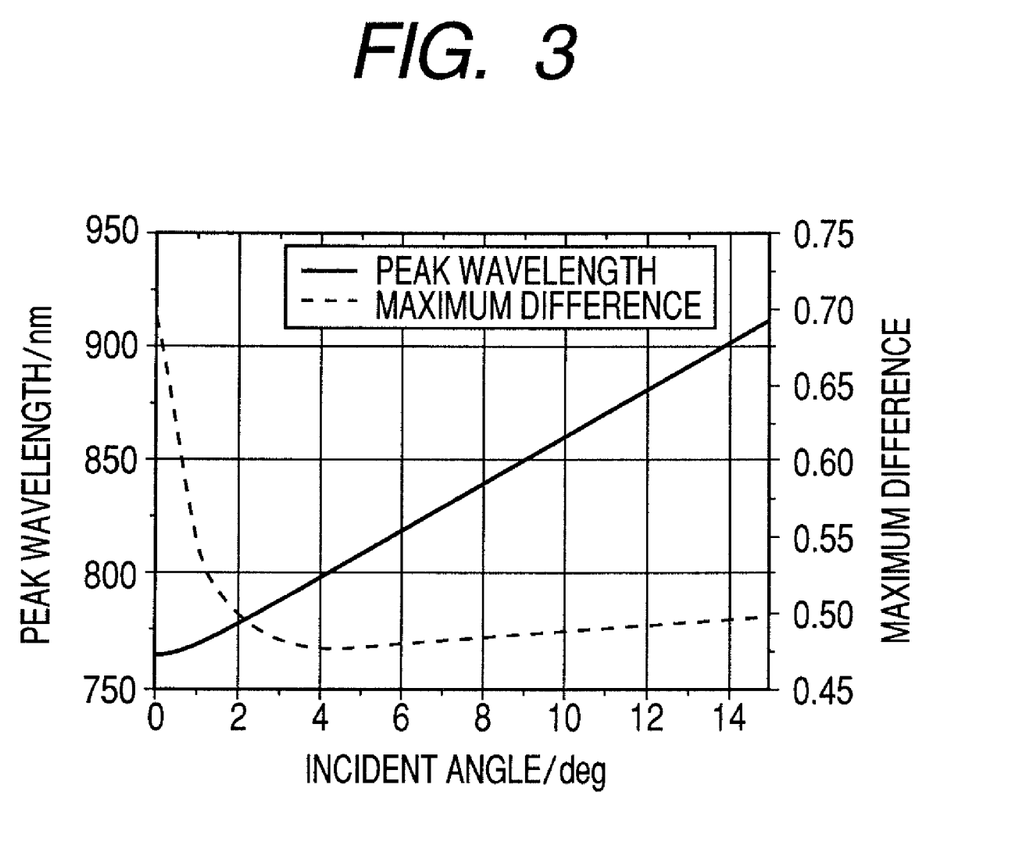
FIG. 3 is a graph illustrating incident angle dependences of the resonance peak wavelength and sensor sensitivity with respect to the metallic fine periodic structure having $\Lambda$=500 nm, f=0.9 and h=80 nm.

FIG. 3 illustrates incident angle dependences of the plasmon resonance peak wavelength (solid line) and the sensor sensitivity (broken line) with respect to the above-described structure.

A phenomenon in which the peak of plasmon resonance shifts to a longer wavelength with increase in incident angle can be described from equations (1) and (2). According to analysis of equation (2), the peak wavelength changes on the order of $n_{in}\Lambda$ with respect to a unit incident angle change (10 nm per 1°). As can be understood from FIG. 3, the sensor sensitivity decreases abruptly to about 70% of the maximum when the incident angle changes by 2 to 3°.

Figure 4A:
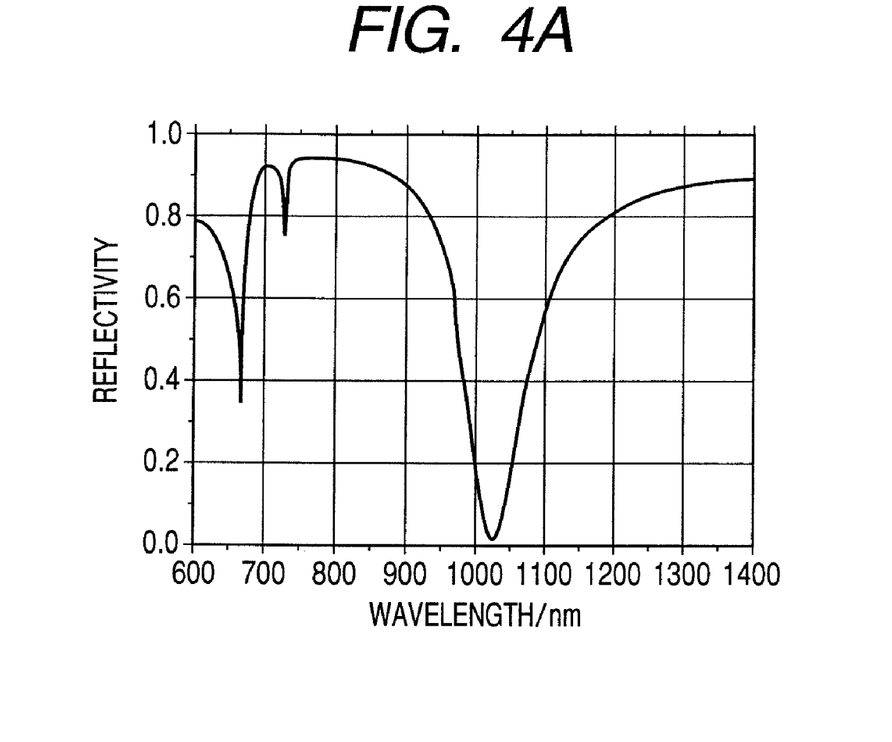
FIG. 4A is a graph illustrating a reflection spectrum with respect to direct incidence on a metallic fine periodic structure having $\Lambda$=500 nm, f=0.9 and h=200 nm.
Figure 4B:
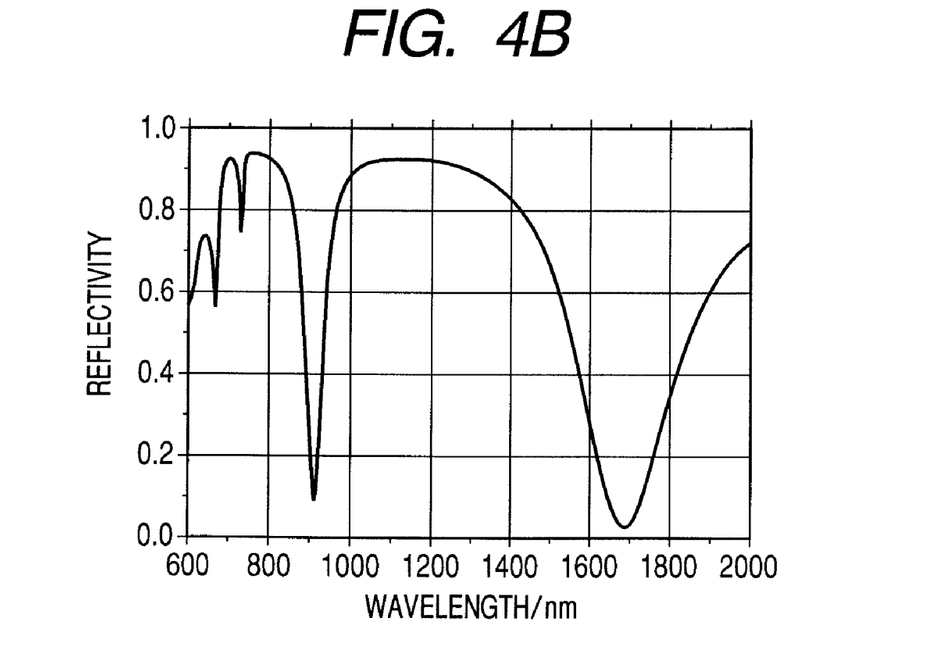
FIG. 4B is a graph illustrating a reflection spectrum with respect to direct incidence on a metallic fine periodic structure having $\Lambda$=500 nm, f=0.9 and h=400 nm.

An example of the present invention will now be described in which a large change in sensitivity with respect to the incident angle, such as that described above, is prevented. In the example of the present invention, the depth of the slits is increased (h=200, 400 nm, aspect ratio q=4, 8) while the same $\Lambda$ and f: $\Lambda=500$ nm, f=0.9 as those in the above-described comparative example are maintained. FIGS. 4A and 4B respectively illustrate the results of computation of reflection spectrums with respect to these values in the case of direct incidence.

As can be understood from FIG. 4A, the peak wavelength is shifted to about 1040 nm in the case where h=200 nm. As can be understood from FIG. 4B, the peak wavelength is further shifted to about 1700 nm in the case where h=400 nm, and a second resonance peak appears at about 910 nm.

Figure 5A:
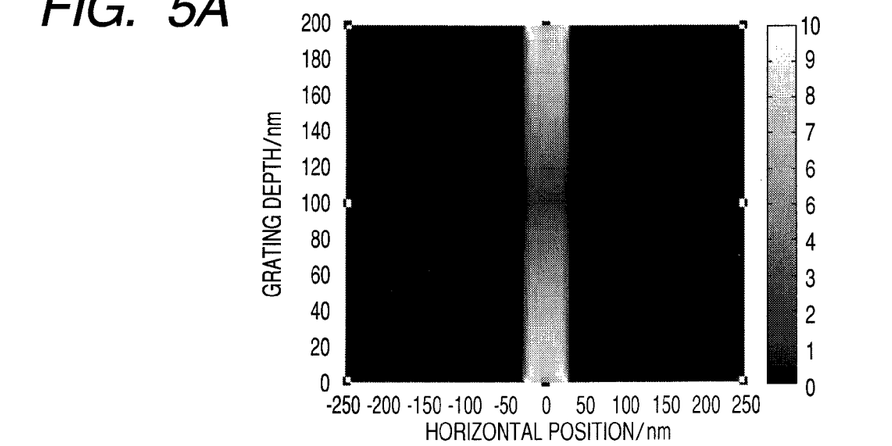
FIG. 5A is a diagram illustrating the magnitude of $E_x$ in a case where $\Lambda$=500 nm, f=0.9, h=200 nm and $\lambda$=1020 nm.
Figure 5B:
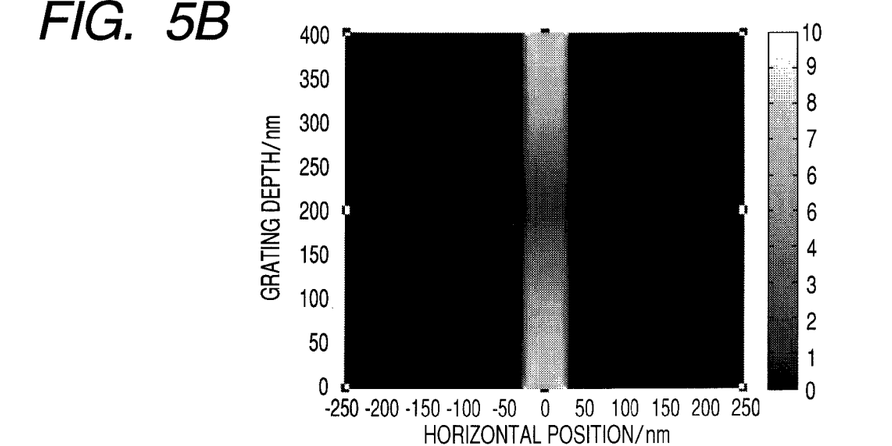
FIG. 5B is a diagram illustrating the magnitude of $E_x$ in a case where $\Lambda$=500 nm, f=0.9, h=400 nm and $\lambda$=1680 nm.
Figure 5C:
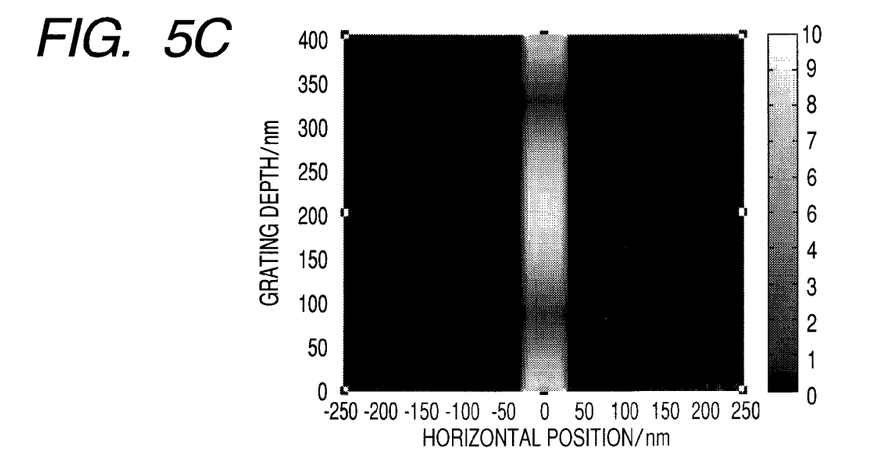
FIG. 5C is a diagram illustrating the magnitude of $E_x$ in a case where $\Lambda$=500 nm, f=0.9, h=400 nm and $\lambda$=910 nm.

FIGS. 5A, 5B and 5C are diagrams illustrating, for description of these peak shifts, the magnitudes of electric field $E_x$ obtained by computing electromagnetic field distributions at the peak wavelengths. It can be understood that as a result of oozing-out into the slit and coupling of plasmons in the slit inner walls in each case, coupling to an incident flat wave is facilitated by flattening of the electric field intensity in the slit and maximization of the electric field intensity at the slit ends. Since the plasmons are compression waves of charges, the electromagnetic energy of the system is reduced by coupling between the plasmons in the inner walls opposed to each other and a red shift of the resonance wavelength results. It can be easily understood that resonance in the secondary mode is caused in the structure having h=400 nm, because two nodes exist along the slit depth direction with respect to the peak at the wavelength 910 nm.

Figure 6:
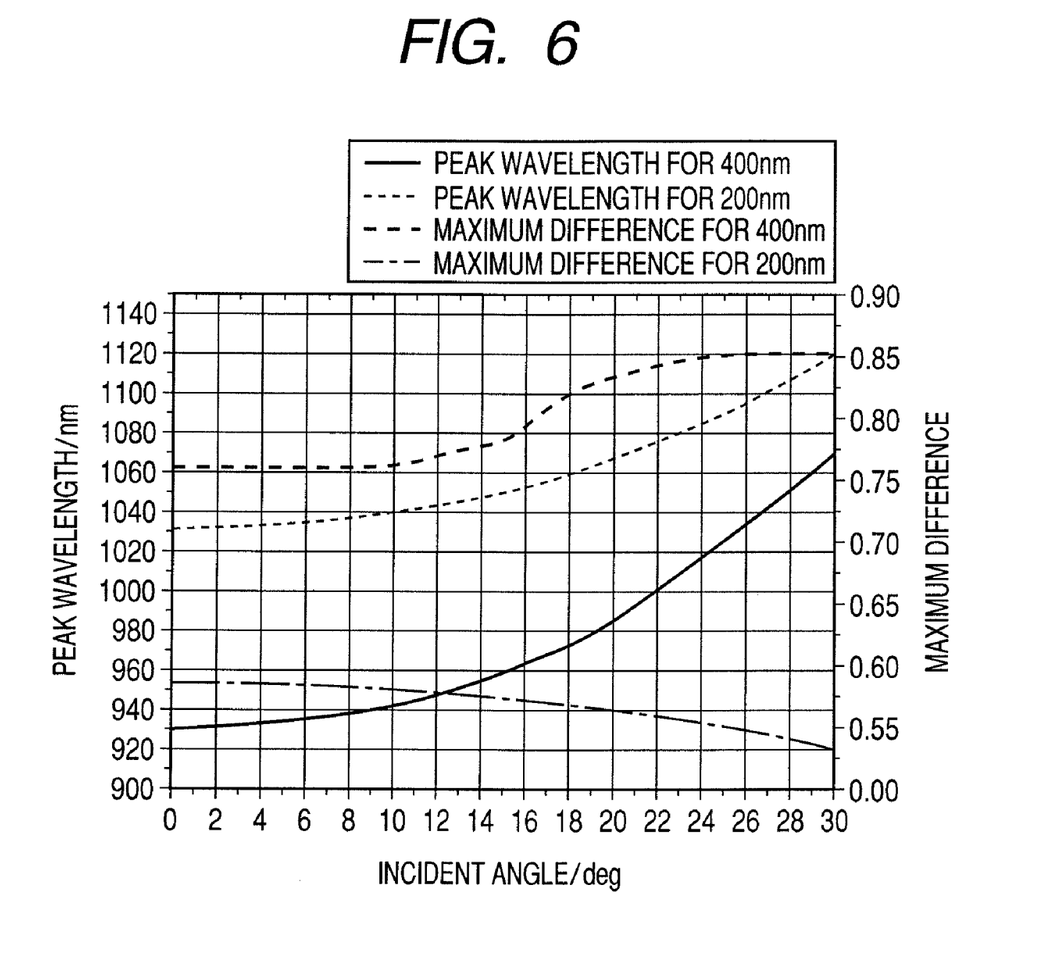
FIG. 6 is a graph illustrating incident angle dependences of the resonance peak wavelength and sensor sensitivity with respect to the metallic fine periodic structure having $\Lambda$=500 nm, f=0.9 and h=200 nm/400 nm.

FIG. 6 is a diagram illustrating the results of computation of incident angle dependences of the peak wavelength and the sensor sensitivity with respect to these resonance peaks performed in the same way as described above. Attention was paid only to the peak at the wavelength 910 nm (secondary coupled plasmon) with respect to the structure having h=400 nm. In a case where the aspect ratio is high and coupled plasmons in the slit inner walls are formed, the coupled plasmon resonance wavelength is determined mainly by the structure. It can be understood that, for this reason, the incident angle dependence becomes about ⅒ (10 nm per 10°) in each of the case where h=200 nm (aspect ratio 4) and the case where h=400 nm (aspect ratio 8) in comparison with the above-described case where h=80 nm (aspect ratio 1.6). That is, an aspect ratio in the range from 4 to 8 is particularly preferable.

Also, since the slit width is sufficiently small, the angle dependence of the efficiency of coupling between incident light and coupled plasmons is weak. Even when the incident angle is increased, no considerable deterioration in sensor sensitivity is observed.

With increase in the incident angle, an overlap between the resonance wavelengths of coupled plasmons in the slit and propagation-type surface plasmons occurs. These plasmons start coupling each other. The resonance wavelength of this new coupled plasmon mode becomes dependent on the incident angle.

This is independent of the aspect ratio (see FIG. 6). However, the spectrum width in the coupled plasmon mode is wider than that of propagation-type surface plasmons and is about ×5. Therefore the substantial wavelength dependence of coupled plasmons is weak.

The angular range in which the incident angle dependence of the resonance wavelength is not considerably large depends on a sufficient shift of the resonance peak of coupled plasmons to a longer wavelength in the case of direct incidence.

Figure 7:
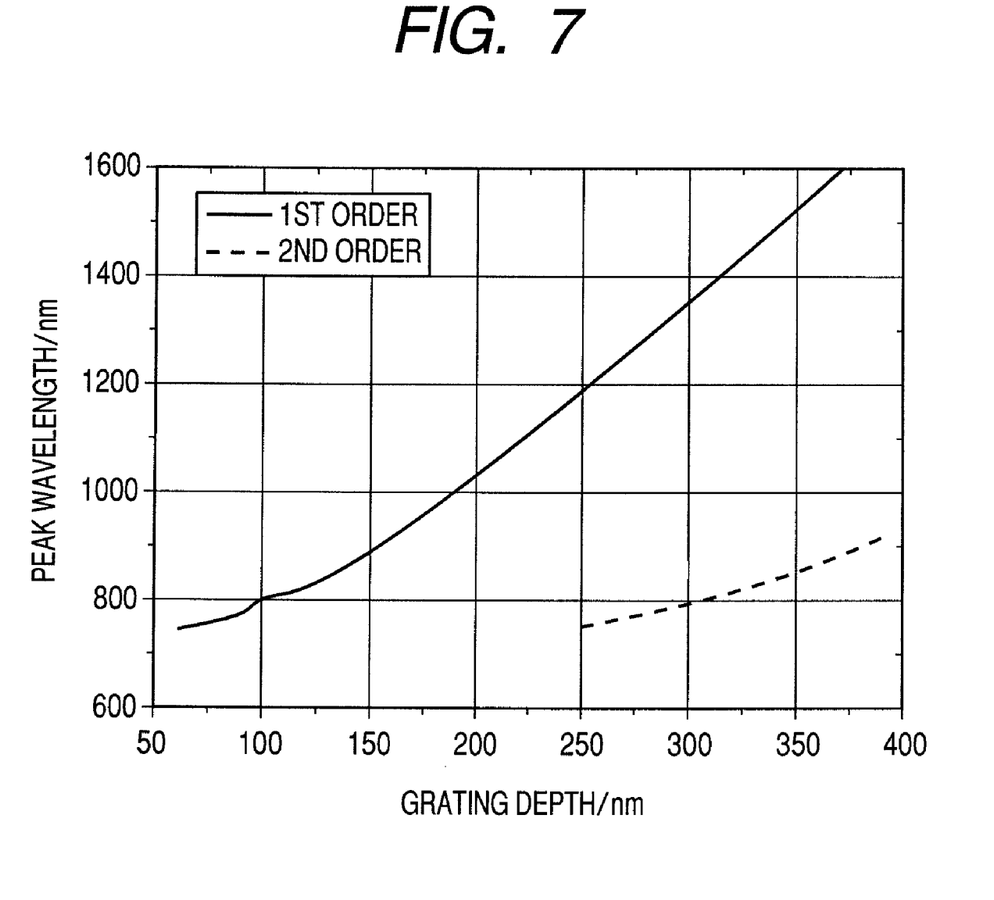
FIG. 7 is a graph illustrating the relationship between the resonance wavelength and the slit depth in the structure having $\Lambda$=500 nm and f=0.9.

This is because the resonance of propagation-type surface plasmons is shifted to a longer wavelength with increase in incident angle according to equations (1) and (2). The shift of the resonance wavelength of propagation-type surface plasmons per unit angle is 10 nm per 1°, as mentioned above. It can, therefore, be said that if the resonance wavelength of coupled plasmons is shifted by 100 nm relative to the resonance wavelength of propagation-type surface plasmons in the case of direct incidence, any considerable peak wavelength shift is not observed in the ±10° incident angle range. FIG. 7 illustrates changes in resonance wavelength when the slit depth is changed while $\Lambda=500$ nm and f=0.9. It can be understood that with respect to the resonance wavelength of primary coupled plasmons a shift of the peak wavelength by 100 nm is achieved at an aspect ratio of 3 or higher.

On the other hand, referring to FIG. 6, the sensor sensitivity increases with the incident angle in the structure having h=400 nm (aspect ratio 8) and becomes maximized at about $\theta$ to 25°. Such an effect is not noticeably observed when h=200 nm (aspect ratio 4). This is for the following reason. In the case of oblique incidence, propagation-type plasmons are produced on the substrate side and in the surface on the sensing medium side. However, when secondary coupled plasmons exist in the slit, these plasmons are in phase with each other, so that the plasmon electric field is further strengthened with respect to the incident waves.

From the foregoing, according to the present example: (1) A sensor of a direct incidence configuration having a reduced deterioration in each of the resonance wavelength and the sensor sensitivity with respect to a change in incident angle, and (2) a sensor having the angle dependence of the resonance wavelength reduced substantially largely by setting the incident angle at about 25°, and having improved sensitivity and a reduced angle dependence of the sensitivity can be constructed.

Selection from a direct incidence configuration and an oblique incidence configuration having the incident angle set to a finite angle (particularly about 25°) can be made according to a measuring purpose. As a result, a sensor apparatus having an improved degree of freedom with which an illumination optical system is designed and having an increased alignment tolerance margin can be implemented.

As a combination of a light source and a detector, a white light source and a spectrograph or a laser having an oscillation wavelength at a maximum of a differential spectrum and a photodiode may be used. Further, an incident-angle-variable configuration may be made adaptable by means of a combination of a wavelength-variable light source and a photodiode. Lock-in detection or the like for noise reduction by an integration effect may be used in such systems.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-187089, filed Jul. 18, 2007, which is hereby incorporated by reference herein in its entirety.

What is claimed is:

1. A sensor apparatus comprising:
 a sensing element including a metallic member having periodic slit openings and metallic portions, and a substrate on which the metallic member is held;
 a light source which emits light so that the light is incident on the sensing element; and
 a photodetector which detects light obtained from the light source,
 wherein if a period of the slit openings is $\Lambda$; a width of the metallic portions is d; and a thickness of the metallic member is h, then an aspect ratio $h/(\Lambda-d)$ of the slit openings is 3 or higher and an opening width $(\Lambda-d)$ is equal to or smaller than a wavelength of the light applied from the light source to the sensing element.

2. The sensor apparatus according to claim 1, wherein the aspect ratio is within the range from 4 to 8.

3. The sensor apparatus according to claim 1, wherein the opening width $(\Lambda-d)$ is equal to or smaller than $\frac{1}{3}$ of the wavelength of light applied from the light source.

4. The sensor apparatus according to claim 3, wherein the opening width $(\Lambda-d)$ is smaller than 100 nm.

5. The sensor apparatus according to claim 1, wherein the proportion of the metallic portions in the metallic member is equal to or larger than 80% and lower than 90%.

6. The sensor apparatus according to claim 1, wherein the light is introduced from the substrate side of the sensing element.

7. The sensor apparatus according to claim 1, wherein the sensor apparatus utilizes plasmon resonance.

* * * * *